United States Patent [19]

White

[11] Patent Number: 4,956,495
[45] Date of Patent: Sep. 11, 1990

[54] PROCESS FOR PREPARING UNSATURATED NITROGEN CONTAINING ACIDS

[75] Inventor: Woodrow W. White, Akron, Ohio

[73] Assignee: GenCorp. Inc., Fairlawn, Ohio

[21] Appl. No.: 451,660

[22] Filed: Dec. 18, 1989

Related U.S. Application Data

[60] Division of Ser. No. 214,968, Jul. 5, 1988, which is a continuation of Ser. No. 930,485, Nov. 14, 1986, abandoned.

[51] Int. Cl.$^5$ .................................................. C07C 101/30
[52] U.S. Cl. ........................................ 562/567; 560/170
[58] Field of Search ........................... 562/567; 560/170

[56] References Cited

U.S. PATENT DOCUMENTS

| | | |
|---|---|---|
| 3,422,139 | 1/1969 | Talet et al. . |
| 4,289,676 | 9/1981 | Czauderna et al. . |
| 4,443,623 | 4/1984 | Photis . |
| 4,656,308 | 4/1987 | Schirmann et al. . |

FOREIGN PATENT DOCUMENTS

| | | |
|---|---|---|
| 0002254 | 5/1979 | European Pat. Off. . |
| 0020000 | 12/1980 | European Pat. Off. . |
| 0237643 | 9/1987 | European Pat. Off. . |
| 1297598 | 7/1969 | Fed. Rep. of Germany . |
| 2640615 | 3/1977 | Fed. Rep. of Germany . |
| 1103916 | 2/1968 | United Kingdom . |

OTHER PUBLICATIONS

Chem Abstracts, vol. 100, No. 23, June 4, 1984, p. 539, "Alkyl Acrylamidoglycolates and Their Alkyl Esters," American Cyanamid Co.

*Primary Examiner*—Joseph L. Schofer
*Assistant Examiner*—Mark D. Sweet

[57] ABSTRACT

A process for preparing unsaturated nitrogen containing acids such as acrylamidoglycolic acid utilizes a catalyst free route and low pH conditions. An unsaturated amide such as acrylamide is reacted with an aldehyde acid such as acid in an aqueous environment. The unsaturated nitrogen containing acids are typically produced in solution form and can be utilized as such.

5 Claims, No Drawings

PROCESS FOR PREPARING UNSATURATED NITROGEN CONTAINING ACIDS

CROSS REFERENCE

This application is a division of application Ser. No. 07/214,968, filed Jul. 5, 1988, of Woodrow W. White, for "A PROCESS FOR PREPARING UNSATURATED NITROGEN CONTAINING ACIDS," which, in turn, is a continuation of application Ser. No. 06/930,485, filed 11/14/86, now abandoned of Woodrow W. White, for "A PROCESS FOR PREPARING UNSATURATED NITROGEN CONTAINING ACIDS."

FIELD OF THE INVENTION

The present invention relates to the preparation of unsaturated nitrogen containing acids in a salt free form. More specifically, the present invention relates to the production of unsaturated nitrogen containing acids in a low pH salt free solution.

BACKGROUND

Heretofore, unsaturated nitrogen containing acids have been prepared utilizing alkali compounds as a catalyst. The end product was generally a basic salt which required purification as by utilizing an acid, for example hydrochloric, to neutralize the solution containing the end product whereby it was precipitated.

U.S. Pat. No. 3,422,139 relates to the preparation of acrylamidoglycolic acid utilizing an alkali carbonate catalyst and the need to crystalize the product before use thereof.

SUMMARY OF THE INVENTION

It is therefore an aspect of the present invention to provide an in-situ process for the preparation of an unsaturated nitrogen containing acid.

It is still another aspect of the present invention to provide an in-situ process for the preparation of an unsaturated nitrogen containing acid, as above, which eliminates the use of a catalyst and is relatively inexpensive.

It is still another aspect of the present invention to provide an in-situ process for the preparation of an unsaturated nitrogen containing acid, as above, wherein a low pH reaction has a relatively good rate and the product has relatively few impurities.

It is yet another aspect of the present invention to provide an in-situ process for the preparation of an unsaturated nitrogen containing acid, as above, wherein the reaction products which exist in a solution form can be utilized in a latex polymerization.

These and other aspects of the invention will become apparent from the following detailed description.

In general, a process for preparing an unsaturated nitrogen containing acid comprising the steps of adding an unsaturated amide reactant to a vessel, adding an aldehyde acid reactant to a vessel, and reacting said reactants to produce a salt free unsaturated nitrogen containing acid.

DETAILED DESCRIPTION

According to the concepts of the present invention, an in-situ reaction between an unsaturated amide and an aldehyde acid, generally in the presence of a carrier such as water, produces an unsaturated nitrogen containing acid typically in solution form. The unsaturated amide can generally be any compound known to the art and to the literature which will react with an aldehyde acid to produce the product of the present invention. Such amides generally have the formula

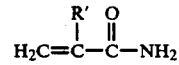

wherein R' is hydrogen, or an alkyl containing 1 to 3 carbon atoms with $CH_3$, that is methyl, being desired.

The aldehyde acid of the present invention generally contains an aldehyde group as well as a carboxylic acid group. Also, within the concepts of the present invention is an ester of the carboxylic acid. Generally, any aldehyde acid which will react with an unsaturated amide to produce the unsaturated nitrogen containing acid product of the present invention can be utilized. Typically, such aldehyde acids have the formula

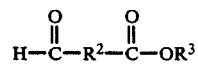

wherein $R^2$ is nonexistant, $CH_2$, $C_2H_4$, and the like. $R^3$ is H when an acid is utilized or is an alkyl substituent having from 1 to 4 carbon atoms when an ester is utilized. Preferably, $R^2$ is nonexistant and $R^3$ is hydrogen.

Although an equivalent amount of the unsaturated amide reactant can be utilized based upon an equivalent of the alhehyde acid, a slight excess is desirable inasmuch as it speeds up the reaction rate. Moreover, since synergistic results with regard to various latex properties are obtained by utilizing an unsaturated amide compound such as acrylamide, it is conveniently added in the preparation of the unsaturated nitrogen containing acid. Hence, an excess of the unsaturated amide reactant is utilized. Accordingly, the amount of unsaturated amide utilized can be from about 0.9 to about 2.5 equivalents, desirably from about 1.2 to about 2.4 equivalents, and preferably from about 1.7 to about 2.0 equivalents for each equivalent of aldehyde acid.

The reaction of the reactants is generally carried out in a reaction medium such as water so that a solution is produced. Although the solution can contain generally any amount of solid, unsaturated nitrogen containing acid product therein, from about 25 to about 70% by weight of solids, desirably from about 30% to about 60% by weight, and preferrably from about 40% to about 55% by weight is preferred based upon the total weight of the solution, that is the weight of the solid acid product and the liquid. The reaction is generally carried out at elevated temperatures with higher temperatures yielding faster reaction rates of the reactants. Accordingly, the reaction temperature is at least 40° C. Since water is generally utilized as the reaction medium, the maximum temperature will be 100° C. unless the reaction is carried out under pressure. A desirable reaction temperature range is from about 60° C. to about 100° C. with from about 70° C. to about 100° C. being preferred. The reaction is generally carried out at atmospheric pressure because of convenience although subatmospheric or superatmospheric pressures can also be utilized.

As noted above, the reaction preferably is conducted without the use of any catalyst, buffer systems, and the like, such that a salt free unsaturated nitrogen containing acid is produced. This method not only produces a product having low impurities, but is also relatively inexpensive since purification is not required. Inasmuch as a basic catalyst and the like are not utilized, the pH of the reaction as well as of the slurry is generally low or acidic and usually is from about 1.0 to about 8.0, desirably from about 1.2 to about 7.0, and preferably from about 1.4 to about 4.0.

Another advantage of the present invention is that since the unsaturated nitrogen containing acid exists in a relatively pure solution, it can be utilized as is, without any purification of the solution, in various latex polymerization reactions well known to the art and to the literature.

The reaction between the unsaturated amide and the aldehyde acid produces an unsaturated nitrogen containing acid of the following formulation

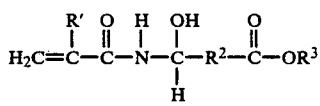

wherein R', R$^2$, and R$^3$, are as set forth hereinabove. Examples of suitable products include methacrylamidoglycolic acid, acrylamido lactic acid, with acrylamidoglycolic acid being preferred. Naturally, various esters thereof can also be utilized wherein R is methyl, ethyl, or butyl, such as methyl acrylamidoglycolate, etc.

Various conventional additives can be utilized during the reaction as known to the art and to the literature such as inhibitors. The inhibitors are utilized to prevent polymerization of the vinyl group in the unsaturated amide. Generally, free radical inhibitors are utilized such as hydroquinone, para-methoxy phenol, and t-butyl catechol. When utilized, the amount of the inhibitors is generally from about 10 to about 1,000 parts by weight, desirably from about 20 to about 500 parts by weight and preferably from about 5 to about 150 parts by weight for each 1 million parts by weight of the reactants.

The unsaturated nitrogen containing acids of the present invention are generally prepared in a suitable vessel, such as a reactor, etc., and subsequently utilized in solution form and added to a solution containing latex forming monomers. Alternatively, the reactants of the present invention can be reacted in-situ in a latex forming vessel. That is, the unsaturated amide and the aldehyde acid can be added to a vessel containing a latex forming monomer solution as the reaction medium and reacted therein while the latex monomers are being polymerized. Upon formation of the unsaturated nitrogen containing acid of the present invention, it will generally react with the latex forming monomers. It is thus to be understood that such in situ preparation is within the scope of the present invention. The latex forming monomers can be any conventional monomers known to the art as well as to the literature and include monomers such as the various conjugated dienes containing from 4 to 10 carbon atoms, the various vinyl substituted aromatics containing from 8 to 12 carbon atoms, such as styrene, and the like.

The invention will be better understood by reference to the following Examples:

EXAMPLE I

This example illustrates the effect of pH of the reaction media on rate of disappearance of glyoxlic acid and the subsequent effect on cure rate of the saturated Whatman paper.

Three reactions were carried out at 50° C. using the following formulations:

|  | A | B | C |
|---|---|---|---|
| 53.7% glyoxylic acid, gms | 94.6 | 94.6 | 94.6 |
| 50% acrylamide, gms | 178 | 178 | 178 |
| 50% sodium hydroxide, gms | 0 | 38.5 | 62.5 |
| pH | 1.6 | 3.5 | 7.0 |

The samples were tested for residual glyoxylic acid each hour with results as follows:

| REACTION TIME - HOURS | RESIDUAL GLYOXYLIC ACID - % | | |
|---|---|---|---|
| 1 | (117.6) | 62.5 | 18.2 |
| 2 | 94.9 | 45.5 | 14.0 |
| 3 | 85.2 | 44.2 | 14.5 |
| 4 | 66.4 | 32.2 | 13.1 |
| 5 | 48.2 | 37.5 | 11.6 |
| 6 | 40.5 | 24.3 |  |
| Overnight | 27.3 | 23.4 |  |

It is apparent that the test method should have been recalibrated since A after 1 hour is still greater than 100%. However, it is clear that the reaction is accelerated at higher pH's.

| CHEMICAL DEFINITIONS: | |
|---|---|
| Hampene Na-3 | A 38% aqueous solution of Trisodium ethylene diamine tetra acetate W. R. Grace & Co. |
| Dowfax 2A-1 | Light colored liquid containing 45% minimum active ingredients in water of sodium dodecyl diphenyl oxide disulfonate C$_{12}$H$_{25}$C$_{12}$H$_7$O (SO$_3$Na)$_2$ The Dow Chemical Co., an anionic surfactant |
| Aerosol MA | Bis(1-methylamyl) sodium sulfosuccinate $$CH_3(CH_2)CHOOCC\overset{CH_3}{\underset{H}{-}}\overset{H_2}{C}-\overset{SO_3Na}{\underset{H}{C}}-COOC(CH_2)_3CH_3$$ American Cyanamid Co., an anionic surfactant. 80% in water. |
| Sipex BOS | Sodium 2-ethyl hexyl sulfate $$\overset{H}{\underset{H}{HC-}}\overset{C_2H_5}{\underset{}{C}}-CH_2-CH_2-CH_2-CH_2OSO_3Na$$ |
| Sulfole 120 | Alcolac Inc., 40% aqueous solution. t-dodecyl mercaptan, avg. mol. wt. 198 Calc. purity wt. 96.8% and mercaptan sulfur wt. 15.4% Phillips Petroleum, Co., Rubber Div. |

The test method utilized in the examples for measuring wet tensile strength is as follows:

Whatman #4 chromatographic paper die-cut to 8"×10" is used with a tolerance of ±5.0% in an untreated weight basis. The sheets are saturated with the latex using a laboratory padder at a binder add-on target of 20±1.5% based on the finished sheet weight. The saturated sheets are air dried at room temperature and then duplicate sheets are cured on the steam heated drier cans at 315° F. for 15, 30, 60, and 300 seconds. All sheets are conditioned in accordance with TAPPI test method T402 before testing. Then they are immersed in distilled water until they are completely wetted. The tensile is then determined on four test strips in both the machine direction (MD) and in the cross direction (CD) for each cured sheet. The average of the eight results in each direction and the total tensile is reported as the sum of the DC and MD averages. This result is normalized to a basis weight of 73.0 lbs./300 ft. and a binder add on of 20%.

EXAMPLE II

Each of the products in Example 1 was used at 7 PHM in polymerization of latexes in bottles as detailed below. In each case an initial charge was made to the bottles using the ingredients in the order listed in the table. The bottles were flushed with nitrogen, capped, and allowed to react 45 minutes at 65° C.

The bottles were opened, recharged with the appropriate amount of styrene, Sulfole 120, and butadiene as listed in the table. This charge was reacted until the bottles were under vacuum as a result of most of the monomers having reacted.

The bottles were opened a second time and further monomers, Sulfole 120, and the experimental activated acids added as listed. This charge was also reacted to vacuum. The latexes obtained were tested without stripping.

| LATEX | A | B | C |
|---|---|---|---|
| INITIAL CHARGE | | | |
| Water, ml | 68 | 68 | 68 |
| Solution A, ml | 20 | 20 | 20 |
| Solution B, ml | 60 | 60 | 60 |
| Solution C, ml | 18 | 18 | 18 |
| Styrene, gms | 15 | 15 | 15 |
| Reacted 45 minutes at 65° C. | | | |
| FIRST CHARGE BACK | | | |
| Styrene, gms | 34 | 34 | 34 |
| Solution D, gms | 10 | 10 | 10 |
| Butadiene, gms | 40 | 40 | 40 |
| Reacted to vacuum | | | |
| SECOND CHARGE BACK | | | |
| Water, ml | 0 | 57 | 57 |
| Solution E, gms | 93 | 0 | 0 |
| Solution F, gms | 0 | 27 | 0 |
| Solution G, gms | 0 | 0 | 27 |
| Solution C, ml | 10 | 10 | 10 |
| Styrene, gms | 34 | 34 | 34 |
| Solution D, gms | 10 | 10 | 10 |
| Butadiene, gms | 40 | 40 | 40 |
| Reacted to vacuum | | | |

Solution A - 0.5% (W/V) Hampene Na-3, 0.9% (W/V) Dowfax 2A-1, 5.0% (W/V) Sipex BOS, and 3.0% (W/V) Aerosol MA in deionized water
Solution B - 5.0% (W/V) Itaconic acid in deionized water
Solution C - 5.0% (W/V) Sodium persulfate in deionized water
Solution D - 3.8% (W/W) Sulfole 120 in styrene
Solution E - 15.0% (W/V) A from Example 1 in deionized water
Solution F - Product B from Example 1 in deionized water
Solution G - Product C from Example 1 in deionized water

LATEX PROPERTIES

| | A | B | C |
|---|---|---|---|
| Total Solids, % | 43.8 | 44.6 | 44.7 |
| pH | 2.4 | 3.7 | 4.4 |
| Brookfield Viscosity, cps | 43 | 48 | 45 |
| Surface Tension, dynes, cm | 45.7 | 45.7 | 44.7 |

It is evident that the three latexes have different pH's as a result of the differences in pH of the reaction to form the products as shown in Example 1.

Each of the latexes were tested in Whatman #4 paper with the following results:

| CURE TIME - SECONDS | | NWTT | |
|---|---|---|---|
| 15 | 24.6 | 18.3 | 15.0 |
| 30 | 27.1 | 23.2 | 18.8 |
| 60 | 28.7 | 26.6 | 22.4 |

Example A relates to the present invention in that no basic catalyst such as sodium hydroxide was utilized. In contrast, Examples B and C relate to the prior art method of utilizing a basic catalyst. Even though the reaction between glyoxylic acid and acrylamide is promoted by a high pH, the above data indicates that such increased pH results in poor latex performance. Thus, the product of the present invention produces better properties on the Whatman #4 paper test than the same prior art solution made with sodium hydroxide.

EXAMPLE III

This example shows the preparation of a product at 49.5 percent total solids and having a mole ratio of 1:1.8 of glyoxylic acid to acrylamide. This product when used in an emulsion polymerization recipe at 7 PHM would be theoretically equivalent to 5 PHM of acrylamidoglycolic acid and 2 PHM of acrylamide.

Three (3) polymerization bottles were each charged with 143.5 grams (1.03 moles) of 53.3% (W/W) of glyoxylic acid, 267 grams (1.88 moles) of 50.0% (W/W) of acrylamide, and 17.5 grams (25 PPM on AGA) of a 0.03% (W/V) solution of paramethoxy phenol in deionized water. The bottles were rotated in a polymerization bath at 170° F. for five (5) hours. Alternate bottles were tested for residual glyoxylic acid at 1½ hour intervals with the results of 34.9, 28.8, and 18.4 percent respectively. The contents of the bottles were blended and stored in a refrigerator.

It is noted that the theoretical total solids content of this product is 49.5 percent. The commercial product acrylamidoglycolic acid monohydrate is only soluble at about 13 percent. The reason for this wide discrepancy in solubility is unknown but the greater solubility of the product of the present invention is a significant commercial advantage since it enables preparation of latexes having a high solids content.

EXAMPLE IV

The product prepared in Example III was used at 3, 5, and 7 PHM, in polymerization of latexes in one gallon reactors equipped with stirrer, heating and cooling means, charging and discharging means, and temperature controller. The reactor was purged with nitrogen before use and the polymerization was conducted under nitrogen.

| PROCESS | | |
|---|---|---|
| A. INITIAL CHARGE TO REACTOR (Same for Latexes A, B, and C) | AS IS PARTS | PURE PARTS |
| Water | 88.7 | 90.0 |
| Hampene Na-3 | 0.132 | 0.05 |
| Dowfax 2A-1 | 0.567 | 0.085 |
| Sipex BOS | 1.18 | 0.5 |
| Aerosol MA | 0.375 | 0.3 |
| Itaconic Acid | 1.5 | 1.5 |
| Sodium Persulfate | 0.45 | 0.45 |
| Styrene | 7.5 | 7.48 |
| Line temperature out at 65° C. and pull vacuum | | |
| React 45 minutes | | |

| PROCESS | | | | | | |
|---|---|---|---|---|---|---|
| B. FIRST MONOMER | A | | B | | C | |
| CHARGE | AS IS | PURE | AS IS | PURE | AS IS | PURE |
| Styrene | 7.333 | 7.311 | 7.666 | 7.643 | 8.000 | 7.976 |
| Sulfole 120 | 0.063 | 0.063 | 0.063 | 0.063 | 0.063 | 0.063 |
| Butadiene | 6.667 | 6.647 | 6.667 | 6.647 | 6.667 | 6.647 |
| React to about 75% conversion of monomers | | | | | | |
| C. Second Monomer Charge (Same as First) | | | | | | |
| D. Third Monomer Charge (Same as First and Second) | | | | | | |
| E. Fourth Monomer Charge | | | | | | |
| Water | 9.64 | 12 | 10.32 | 12 | 10.99 | 12 |
| Example 3 | 4.67 | 2.31 | 3.33 | 1.65 | 2.00 | 0.99 |
| Styrene | 7.333 | 7.311 | 7.666 | 7.643 | 8.000 | 7.976 |
| Sulfole 120 | 0.063 | 0.063 | 0.063 | 0.063 | 0.063 | 0.063 |
| Butadiene | 6.667 | 6.647 | 6.667 | 6.647 | 6.667 | 6.647 |
| React to 75% conversion of monomers | | | | | | |
| F. Fifth Monomer Charge | | | | | | |
| Water | 9.64 | 12 | 10.32 | 12 | 10.99 | 12 |
| Example 3 | 4.67 | 2.31 | 3.33 | 1.65 | 2.00 | 0.99 |
| Water | 2.75 | 3 | 2.75 | 3 | 2.75 | 3 |
| Sodium persulfate | 0.25 | 0.25 | 0.25 | 0.25 | 0.25 | 0.25 |
| Styrene | 7.333 | 7.311 | 7.666 | 7.643 | 8.000 | 7.976 |
| Sulfole 120 | 0.063 | 0.063 | 0.063 | 0.063 | 0.063 | 0.063 |
| Butadiene | 6.667 | 6.647 | 6.667 | 6.647 | 6.667 | 6.647 |
| React to 75% conversion of monomer | | | | | | |
| G. Sixth Monomer Charge (Same as fifth) | | | | | | |
| React to constant solids plus one hour | | | | | | |
| H. Post Polymerization - Short Stop for Each Batch | AS IS | | | PURE | | |
| Water | 2.974 | | | 3 | | |
| Diethylhydroxyl Amine | 0.176 | | | 0.15 | | |

All latexes were stable during polymerization and had the following properties:

| | A | B | C |
|---|---|---|---|
| Total Solids, % | 41.9 | 41.9 | 43.1 |
| pH | 2.7 | 2.5 | 2.7 |
| Viscosity Brookfield, cps | 173 | 39 | 20 |
| Surface Tension, dynes, cm | 48.6 | 49.6 | 47.6 |

The latexes were used to saturate Whatman #4 chromatographic paper as described in the Test Method for measuring wet tensile development and the results are set forth in the following table. Results obtained with a conventional commercial latex (D).

| | NWTT 2 73# & 20.0% | | | |
|---|---|---|---|---|
| Cure Time, Seconds | A | B | C | D |
| 15 | 28.0 | 26.4 | 22.7 | 12.0 |
| 30 | 29.6 | 26.1 | 24.9 | 15.1 |
| 60 | 31.9 | 30.8 | 26.3 | 17.4 |
| 300 | 36.1 | 32.2 | 28.0 | 20.9 |
| GENERAL FUNCTIONAL COMPOSITION, PHM | | | | |
| Example 3 | 7 | 5 | 3 | 0 |
| Acrylamidoglycolic Acid | 0 | 0 | 0 | 0 |
| Acrylamide | 0 | 0 | 0 | 0 |
| THEORETICAL EQUIVALENTS | | | | |
| | A | B | C | D |
| Acrylamidoglycolic Acid | 5 | 3.6 | 2.1 | 0 |
| Acrylamide | 2 | 1.4 | 0.9 | 0 |

The superior results for the latexes of this invention are clearly evident by comparing the results for A, B, and C with that of D. Latex C which contains only 3 PHM of the experimental reactive acid gave wet tensiles about 80 percent higher than those with the commercial latex D. Latex A which contains 7 PHM of the experimental reactive acid gave results about 126 percent higher than that of the commercial latex D.

While in accordance with the Patent Statutes, a preferred embodiment and best mode has been set forth, the scope of the invention is not limited thereto, but rather by the scope of the attached claims.

What is claimed is:

1. A process for preparing an unsaturated nitrogen containing acid, comprising the steps of:
   adding an unsaturated amide reactant to a vessel, said unsaturated amide having the formula

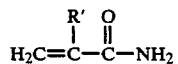

where $R^1$ is H, or an alkyl having from 1 to 3 carbon atoms,
   adding an aldehyde acid reactant to said vessel, said aldehyde acid having the formula

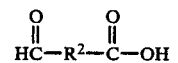

where $R^2$ is nonexistent, $CH_2$, or $C_2H_4$, where the equivalent amount of said amide to said acid is from about 1.2 to about 2.4 equivalents, and
   reacting said reactants in the presence of an acidic aqueous reaction medium having a pH of from about 1.2 to less than 7.0 and producing a salt free unsaturated nitrogen containing acid, said unsaturated nitrogen containing acid having the formula

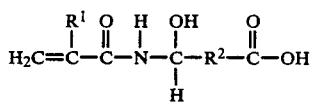

wherein $R^1$ is H, or an alkyl having from 1 to 3 carbon atoms, wherein $R^2$ is nonexistent, $CH_2$, or $C_2H_4$.

2. A process according to claim 1, wherein said reaction temperature is from about 60° C. to about 100° C., and wherein $R^2$ is nonexistent.

3. A process according to claim 2, wherein said reaction temperature is from about 70° C. to about 100° C., wherein said pH is from about 1.4 to about 4.0, and wherein R' is H.

4. A process according to claim 3, wherein said equivalent amount of said amide to said acid is from about 1.7 to about 2.0, and including utilizing a sufficient amount of said aqueous reaction medium so that a solution containing from about 25 percent to about 70 percent by weight of said unsaturated nitrogen containing acid compound is produced.

5. A process according to claim 3, including utilizing a sufficient amount of said aqueous reaction medium so that a solution containing from about 40 percent to about 55 percent by weight of said unsaturated nitrogen containing acid compound is produced.

* * * * *